United States Patent [19]

Wakashiro et al.

[11] Patent Number: 5,212,201

[45] Date of Patent: May 18, 1993

[54] XANTHINE OXIDASE INHIBITOR

[75] Inventors: Michio Wakashiro, Kyoto; Shiro Abe, Ayabe; Nobukazu Tanabe, Ayabe; Hiroshi Obata, Ayabe, all of Japan

[73] Assignee: Gunze Limited, Kyoto, Japan

[21] Appl. No.: 612,144

[22] Filed: Nov. 13, 1990

[30] Foreign Application Priority Data

Nov. 20, 1989 [JP] Japan .................................. 1-302818

[51] Int. Cl.$^5$ .......................................... A01N 37/10
[52] U.S. Cl. .............................. 514/532; 560/75
[58] Field of Search ........................ 560/75; 514/532

[56] References Cited

PUBLICATIONS

Arihara, S. et al Helv. Chim. Acta vol. 58 (2) pp. 447-453 1975.

*Primary Examiner*—Paul J. Killos
*Attorney, Agent, or Firm*—Wenderoth, Lind & Ponack

[57] ABSTRACT

A pharmaceutical composition inhibiting xanthine oxidase containing as an active component a compound of the formula:

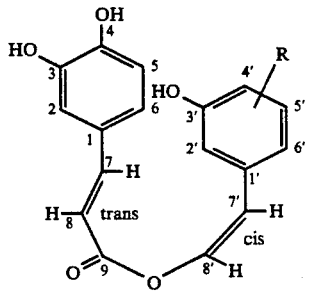

wherein R is 4'-OH or 5'-OH, or a pharmaceutically acceptable salt or ester thereof is disclosed. The compound wherein R is 5'-OH is a novel compound.

3 Claims, No Drawings

XANTHINE OXIDASE INHIBITOR

FIELD OF THE INVENTION

The present invention relates to a novel pharmaceutical composition for inhibiting xanthine oxidase and a novel compound having xanthine oxidase inhibitory activity which is useful for the active component of the pharmaceutical composition.

BACKGROUND OF THE INVENTION

Uric acid which is a pathogenic substance of gout is synthesized by xanthine oxidase in the human body. Accordingly, inhibition of xanthine oxidase is useful for treatment and prevention of gout. In fact, allopurinol which is known as a therapeutic drug for gout is a useful xanthine oxidase inhibitor.

The present inventors have studied xanthine oxidase inhibitors contained in edible plants, and found that a component having xanthine oxidase inhibitory activity is present in edible plants of Labiatae, Compositae and Liliaceae, and an extract of these plants is useful for treating hyperuricemia. The present inventors have filed a patent application directed to a pharmaceutical composition for improving hyperuricemia comprising as an active component an extract from these plants (Japanese patent application no. 1-213998).

The present inventors have further studied the above active component and have succeeded in isolation and purification of active compounds from plants of Labiatae.

OBJECTS OF THE INVENTION

One object of the invention is to provide a novel pharmaceutical composition for inhibiting xanthine oxidase for treatment or prevention of gout.

Another object of the present invention is to provide a novel compound having xanthine oxidase inhibitor activity.

These objects as well as other objects and advantages of the present invention will become apparent to those skilled in the art from the following description.

SUMMARY OF THE INVENTION

According to the present invention, there is provided a pharmaceutical composition inhibiting xanthine oxidase which comprises as an active component a compound of the formula I:

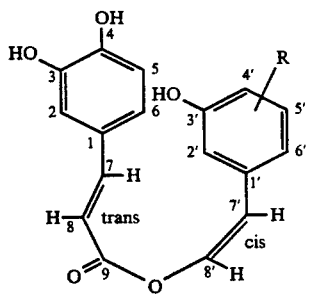

[I]

wherein R is 4'-OH or 5'-OH, or a pharmaceutically acceptable salt or an ester thereof.

The compound of the formula [I] wherein R is 5'-OH [I'] is not found in the prior art and is a novel compound. Therefore, the present invention also provides the compound [I'] and its salt.

DETAILED DESCRIPTION OF THE INVENTION

Both active compounds of the formula [I] having xanthine oxidase inhibitory activity used in the present invention have the molecular formula $C_{17}H_{14}O_6$, and they can be named as (Z,E)-2-(3,4-dihydroxyphenyl)ethenylester (abbreviated as XOI-A) or (Z,E)-2-(3,5-dihydroxyphenyl)ethenylester (abbreviated as XOI-B) of 3-(3,4-dihydroxyphenyl)-2-propenoic acid.

These compounds can be isolated and purified from edible plants of Labiatae as a starting material by solvent extraction and chromatography.

Examples of the plants of Labiatae to be used as the starting material include perilla, oregano, thyme, basil, sage and the like. These plants have been cultivated and served as food. In the present invention, all the parts thereof including roots, leaves, stems and the like can be used as the starting material.

For isolation and purification, the starting material is firstly extracted with an alcohol such as methanol, ethanol, n-propanol, iso-propanol or the like, or a solvent such as acetone, ethyl acetate, acetonitrile or the like. Then, the product is purified by passing it through a silica gel column. As an eluent, hexane, benzene, diethyl ether or a mixture thereof can be used. The active fraction thus separated by silica gel column chromatography is further subjected to high performance liquid chromatography to obtain two fractions having xanthine oxidase inhibitory activity. Finally, respective fractions are recrystallized from a mixture of water and ethanol or the like to obtain purified XOI-A and XOI-B.

The active compound XOI-A thus isolated and purified is yellow fine crystals having the melting point of 183° to 185° C. (decomp.). On the other hand, XOI-B is yellow needles having the melting point of 188° to 190° C. Both compounds are readily soluble in methanol, propanol, acetone, ethyl acetate or acetonitrile and slightly soluble in water, chloroform or hexane.

Infrared spectra by KBr method are as follows;
IR $(cm^{-1})$:

XOI-A: 3400 (OH), 1690 ($\alpha,\beta$-unsaturated ester), 1625 (phenyl conjugated double bond), 1605 (phenyl ring), 1270, 1150 (ester C-O stretching vibration).

XOI-B: 3380 (OH), 1720 ($\alpha,\beta$-unsaturated ester), 1625 (phenyl conjugated double bond), 1600 (phenyl ring), 1280, 1140 (ester C-O stretching vibration).

Both XOI-A and XOI-B have phenolic OH groups, they can form a salt with an alkali metal and the like, or an ester with an organic or inorganic acid. These salts and esters are within the scope of the present invention.

Both compounds have excellent xanthine oxidase inhibitory activity. This xanthine oxidase inhibitory activity can be determined, for example, as follows:

Sample solution: A sample solution is prepared by dispersing the active compound in a suitable amount of water.

Enzyme solution: An enzyme solution is prepared by dissolving 150 μl of xanthine oxidase (15.2 units/ml) in 10 ml of 1/15 M phosphate buffer (pH 7.5).

Substrate solution: A substrate solution is prepared by heating 22.8 mg of xanthine in 1 liter of water to dissolve it.

Determination: 0.1 ml of the enzyme solution and 2.9 ml of phosphate buffer (the same as that described above) are admixed with 1.0 ml of the sample solution and the mixture is incubated at 37° C. for 10 minutes.

Then, 1 ml of the substrate solution preincubated at 37° C. is added to this reaction mixture and, after reaction for 30 minutes, an absorbance at 290 nm ($D_1$) is measured.

Separately, an absorbance at 290 nm ($D_2$) of a reaction mixture obtained by the similar reaction procedure using a heat inactivated enzyme, an absorbance ($D_3$) without addition of the sample solution, and and absorbance ($D_4$) of a reaction mixture obtained by using a heat-inactivated enzyme without addition of the sample solution are measured. By using the values obtained by these measurements, the inhibitory rate of xanthine oxidase is calculated by using the following equation:

Inhibitory Rate
$(\%) = \{1 - (D_1 - D_2)/(D_3 - D_4)\} \times 100$

According to this method, concentrations required for realizing a 50% inhibitory rate of XOI-A, XOI-B as well as known xanthine oxidase inhibitors, allopurinol, luteolin and quercetin were measured. The results are shown in Table 1.

TABLE 1

| Compounds | Concentration for 50% inhibitory rate (μg/ml) | Relative intensity |
|---|---|---|
| XOI-A | 0.021 | (1.00) |
| XOI-B | 0.124 | (0.17) |
| Allopurinol | 0.021 | (1.00) |
| Luteolin | 0.11 | (0.19) |
| Quercetin | >0.40 | (<0.05) |

As seen from Table 1, the active compound XOI-A of the present invention has an activity comparable to that of allopurinol, and the activity of XOI-B is almost the same as that of luteolin. And, the activities of both XOI-A and B are superior to that of quercetin.

XOI-A and the novel compound XOI-B of the present invention or a pharmaceutically acceptable salt thereof obtained by the conventional method can be formulated into unit dosage forms such as tablets, capsules, pills, powder, granules, powdery packet, cachets, sterile solutions or suspensions, eye drops, elixir, suppository, aerosol, emulsions and the like according to the conventional methods.

For oral administration, they can be formulated into solid or liquid unit dosage forms. For preparing solid compositions, the active compound is mixed with an excipient or carrier such as talc, magnesium stearate, dicalcium phosphate, magnesium aluminum silicate, calcium sulfate, starch, lactose, acacia, methyl cellulose and the like. A capsule is prepared by mixing the active compound with an inert pharmaceutical excipient, filling the mixture into a suitably sized hard gelatin capsule. A soft gelatin capsule is prepared by mechanically encapsulating a slurry of the compound and a suitable vegetable oil, light petrolatum or other inert oil.

For preparing liquid compositions, the active compound is dissolved in an aqueous vehicle together with sugar, an aromatic flavor and a preservative to obtain syrup. An elixir agent is prepared by using an alcoholic vehicle such as ethanol, a sweetener such as sugar or saccharin, and a flavor. A suspension is prepared by using a suspending agent such as acacia, tragacanth, or methyl cellulose, and an aqueous vehicle.

For parenteral administration, a liquid unit dosage form is prepared by using the active compound and a sterile vehicle. The active compound is dissolved or suspended in a vehicle, depending upon the particular vehicle, such as water, Ringer's solution or isotonic sodium chloride solution and a particular concentration to be employed. For preparing solutions, the active compound is dissolved in injectable water, sterilized by filtration, and filled into a suitable vial or ampoule and sealed. Advantageously, an adjuvant such as a local anesthetic, a preservative and a buffer is dissolved in a vehicle. Alternatively, the active compound can be formulated into lyophilized powder which has excellent storage stability. This is reconstituted upon use. A parenteral suspension can be prepared by suspending the active compound according to a similar manner. In this case, the active compound can be sterilized by exposing to ethylene oxide before suspending in a sterilized vehicle. Advantageously, a surfactant or wetting agent is added to facilitate dispersion of the active compound.

In addition, the active compound can be formulated into topical application forms in combination with a suitable carrier for topical application. As examples of the carrier to be used, there are cream, ointment, lotion, paste, jelly, spray, aerosol and the like. Further, the active compound can be formulated into rectal suppository forms useful when no other administration route can be used. As examples of a base to be used, there are cacao butter, polyethylene glycol (carbowax), polyethylene sorbitan monostearate and the like.

The pharmaceutical composition inhibiting xanthine oxidase of the present invention as described above can be administered orally, parenterally, by insufflation, rectally, or topically. Parenteral administration includes subcutaneous, intravenous, intramuscular and intranasal administration as well as infusion. The daily dosage of the active compound is in the range of 0.1 to 200 mg/kg body weight. Usually, the composition is administered once to five times in a day. However, the exact dosage can be selected from the above range in view of particular age, weight and conditions of a patient as well as dosage route.

By administering the active compound in such a dosage, the pharmaceutical composition of the present invention manifests excellent xanthine oxidase inhibitory activity and, therefore, it is useful for improving hyperuricemia and gout.

By the way, the toxicity of the pharmaceutical composition of the present invention must be very low because its active component is derived from edible plants.

The following Examples further illustrate the present invention in detail but are not to be construed to limit the scope thereof.

EXAMPLE 1

*Perilla frutescens* was used as a starting material. The starting material (3.73 kg, fresh weight) was extracted with ethanol. The resultant ethanolic extract was suspended in water and extracted with ethyl acetate. This extract was purified by passing successively through large, medium and small silica gel columns by using hexane-ethyl acetate (40:60) as an eluent to obtain an active fraction. The eluate was then purified by preparative HPLC to obtain two fractions A and B. Each fraction was recrystallized from water-ethanol (50:50) to obtain 42 mg of XOI-A from the fraction A and 11 mg of XOI-B from the fraction B.

Respective isolation and purification procedures as well as solids content and specific activity (U/mg) at respective steps are summarized in Table 2. In Table 2, 1 U represents the activity required for inhibiting 50% of xanthine oxidase.

TABLE 2

| Steps | Total activity × $10^6$ (U) | | Solids content (mg) | Specific activity (μ/mg) | |
| --- | --- | --- | --- | --- | --- |
| Extract obtained by ethanol extraction | 31.80 | (100) | 151600 | 210 | (1) |
| Ethyl acetate layer | 33.30 | (105) | 53350 | 624 | (3) |
| Silica gel column (large) | 15.00 | (47) | 6000 | 2500 | (12) |
| Silica gel column (medium) | 13.40 | (42) | 1780 | 7520 | (36) |
| Silica gel column (small) | 9.17 | (29) | — | — | (—) |
| Preparative HPLC (ODS) | 5.71 | (18) | 150 | 38100 | (181) |
| Fraction A (recrystallization) | 1.96 | (6) | 42 | 46600 | (222) |
| Fraction B (recrystallization) | 0.09 | (—) | 11 | 8040 | (38) |

EXAMPLE 2

Tablets containing XOI-A as an active component were prepared by the conventional method according to the following formulation:

| Ingredient | Parts by weight |
| --- | --- |
| XOI-A | 10 |
| Lactose | 60 |
| Starch | 27 |
| Talc | 1.5 |
| Magnesium stearate | 1.5 |

What is claimed is:

1. A method of inhibiting xanthine oxidase in a patient, which comprises administering to a patient requiring such inhibitory activity a compound of the formula:

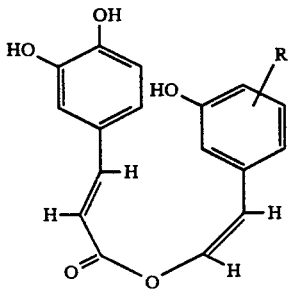

wherein R is 4'-OH or 5'-OH or a pharmaceutically acceptable salt or an ester thereof.

2. A method according to claim 1, wherein R of the compound is 4'-OH.

3. A method according to claim 1, wherein R of the compound is 5'-OH.

* * * * *